US008480579B2

(12) United States Patent
Serov et al.

(10) Patent No.: US 8,480,579 B2
(45) Date of Patent: Jul. 9, 2013

(54) INSTRUMENT AND METHOD FOR HIGH-SPEED PERFUSION IMAGING

(75) Inventors: Alexandre Serov, Lausanne (CH); Theo Lasser, Denges (CH)

(73) Assignee: Ecole Polytechnique Fédérale de Lausanne (EPFL), Lausanne (FR)

( * ) Notice: Subject to any disclaimer, the term of this patent is extended or adjusted under 35 U.S.C. 154(b) by 946 days.

(21) Appl. No.: 11/912,224

(22) PCT Filed: Apr. 20, 2006

(86) PCT No.: PCT/IB2006/000940
§ 371 (c)(1),
(2), (4) Date: Oct. 22, 2007

(87) PCT Pub. No.: WO2006/111836
PCT Pub. Date: Oct. 26, 2006

(65) Prior Publication Data
US 2009/0118623 A1     May 7, 2009

(30) Foreign Application Priority Data

Apr. 20, 2005    (WO) .................. PCT/IB2005/051289

(51) Int. Cl.
*A61B 5/05*      (2006.01)
(52) U.S. Cl.
USPC ............................ 600/363; 600/476; 600/478
(58) Field of Classification Search
USPC ......................................... 600/363, 476, 478
See application file for complete search history.

(56) References Cited

U.S. PATENT DOCUMENTS

| 5,267,016 A * | 11/1993 | Meinzer et al. ............... 356/498 |
| 6,045,511 A * | 4/2000 | Ott et al. ....................... 600/504 |
| 6,263,227 B1 | 7/2001 | Boggett et al. |

FOREIGN PATENT DOCUMENTS

WO      03/063677      8/2003

OTHER PUBLICATIONS

Dyck et al. Integrated Arrays of Silicon Photodetectors for Image Sensing. IEEE Transactions on Electron Devices. 15(4): 196-202. 1968.*
Briers, David J, "Laser Doppler, speckle and related techniques for blood perfusion mapping and imaging", Physiological Measurement, Institute of Physics Publishing, vol. 22, No. 4, pp. R35-R66, 2001.
Serov A.et al, "Speckles in laser Doppler blood flowmetry", University of Twente, Faculty of Applied Physics Biophysical Techniques Group, vol. 4242, 2001.

* cited by examiner

*Primary Examiner* — Parikha Mehta
(74) *Attorney, Agent, or Firm* — Oblon, Spivak, McClelland, Maier & Neustadt, L.L.P.

(57) ABSTRACT

A high-speed laser perfusion imaging instrument including a laser source, a detector, a signal-processing unit, data memory, and a screen to display results. A section of a sample surface is illuminated with laser light; reemitted light from the irradiated surface is collected by focusing optics on a 2D array of integrating photodetectors having elements that can be accessed individually or in a pre-defined selection of pixels at high speed. This 2D array measures intensity variations at each individual pixel. Average amplitude and mean frequency of the measured signal contain information about concentration and speed of moving blood cells. For real-time imaging, exposure time is used as a parameter to measure relative perfusion changes. These data are stored and processed with the signal-processing unit to deliver 2D flow maps of the illuminated sample section, and allow a simple overlay between a conventional image and processed flow maps.

18 Claims, 4 Drawing Sheets

INSTRUMENT AND METHOD FOR HIGH-SPEED PERFUSION IMAGING

FIELD OF THE INVENTION

The invention relates to imaging systems and more particularly to a perfusion and blood flow imaging system mainly applied for medical diagnosis.

BACKGROUND OF THE RELATED ART

Laser Doppler Imaging (LDI) is a non-contact imaging modality based on the coherence properties of light. This imaging modality mainly developed thanks to new detector technology, software and the availability of appropriate laser sources. The performance improved steadily over the last two decades from the initial proposals based on a scanning instrument towards a state of the art instrument for medicine mainly due to a parallel imaging instrument based on CMOS array detectors.

LDI is a coherent imaging technique that allows imaging of moving particles especially cells in blood flow with a good discrimination between perfusion, flow velocities and the concentration of moving particles i.e. mainly the key flow parameters of erythrocytes.

In conventional scanning LDI the back reflected light from a biological sample or the skin or the organ is detected with a single point detector. This light contains the coherent superposition of a back reflected component from non-moving parts and a back reflected light component from moving particles which causes detectable light fluctuations and allows the extraction of maps of flow velocities, concentration of flow particles or the so-called perfusion as the product of flow velocity times flow particle concentration.

In parallel LDI, the signal results from the interference or coherent superposition between a coherent back-scattered light field originating from the coherently illuminated sample of non-moving parts and the coherent back-scattered light field from moving particles contained in the illuminated volume. A 2D array of random-pixel-access integrating photo detectors (e.g. integrating CMOS image sensor) is used to measure the intensity variations at each individual pixel. The average amplitude and the mean frequency of the measured signal contain information about concentration and speed of moving blood cells. Finally maps of flow velocities, concentration of flow particles or the so-called perfusion as the product of flow velocity times flow particle concentration can be displayed as an image.

Anomalous changes in peripheral blood flow are known to be an indicator of various health disorders in the human organism. Laser Doppler Perfusion Imaging (LDPI) is an imaging technique successfully used for visualization of two-dimensional (2D) micro-vascular flow-maps in a number of clinical settings including investigations of e.g. peripheral vascular diseases, skin irritants, diabetes, burns and organ transplants. This method is non-invasive because it involves no physical contact; the risk of infection and additional discomfort is completely avoided.

The technical principle is based on the Doppler effect wherein the light scattered by moving particles, e.g. blood cells, leads to a slight frequency shift, which can be measured by a heterodyne detector. A 2D flow map is obtained by means of sequential measurements from a plurality of predetermined points. In classical LDPI systems this is achieved by scanning the area of interest with a narrow collimated or focused laser beam. However this scanning approach is time-consuming and suffers from artifacts caused by the mechanical steering of the probing laser beam. In current commercial available LDPI systems these artifacts are circumvented on an expense of imaging time.

For those skilled in the art an alternative full-field flow imaging techniques using speckle contrast analysis is also known. For real-time full-field imaging, the exposure time is used as a parameter to measure relative perfusion changes by means of laser speckle imaging technique. The advantage of this approach is a fast image acquisition, which is achieved at an expense of spatial resolution. However, the technique can be hardly exploited for flow measurements, where either concentration or speed of moving particles is not known in advance. Both said parameters influence the system response in the same manner, and, generally, the cause of the contrast decay is not obvious. Also the system response is not linear to the velocity since a finite camera integration time influences the measurement.

In order to decrease the imaging time for parallel LDI, a parallel detection scheme has been employed increasing the imaging speed by a factor proportional to the number of channels working in parallel. A 2D matrix of photo-detectors is a suitable detection device for that purpose.

Recently Serov et al. [A. Serov, W. Steenbergen, F. F. M. de Mul, "Laser Doppler perfusion imaging with a complimentary metal oxide semiconductor image sensor", Opt. Left. 25, 300-302 (2002)] suggested a new approach on parallel laser Doppler imaging: a non-integrating true-random-addressing CMOS image sensor was used to detect Doppler signal from a plurality of points on the sample illuminated with a divergent laser beam. Here the mechanical scanning is substituted by the photoelectrical scan resulting in a faster imaging speed.

The use of non-integrating 2D array of photo-detectors for the purpose of laser Doppler has been disclosed in three publications.

A first publication U.S. Pat. No. 6,263,227: "Apparatus for imaging microvascular blood flow". The concept of using a 1D or 2D matrix of conventional photo detectors is described. The imager can work in two modes - scanning or static. In the scanning mode a laser line is projected on the area of interest. The signals from the illuminated areas are detected by 1D matrix of photo detectors. By scanning the illumination laser light over the area of interest, a 2D perfusion map is obtained. In the static mode the whole area of interest is illuminated by an expanded laser beam or by light exiting an optical fiber. The Doppler signal is measured by 2D matrix of photo detectors. Each photo detector has its own electronics for signal processing. A CCD camera is used to observe the object of interest. The perfusion maps are superimposed on the photographic image obtained with the CCD.

A second publication WO03063677: "Laser Doppler perfusion imaging with a plurality of beams" and a third publication GB2413022:" Laser Doppler perfusion imaging using a two-dimensional random access high pixel readout rate image sensor". Here, a structured illumination is used for illuminating a plurality of points or an area of interest. The Doppler signal from the illuminated areas is detected with 2D matrix of non-integrating (direct-access) photo detectors. For the detection, the use of random-access-fast-pixels-readout CMOS image sensor is claimed. A single CMOS image sensor is used for detecting the Doppler signal and to obtain a photographic image of the object of interest.

All previously mentioned publications describe arrays of non-integrating detectors that measure instantaneous changes of the photocurrent through the detector. Besides the fact that both publications disclose imaging systems based on integrating detectors, both documents use a true laser Doppler technique to measure the flow.

Laser speckle imaging (LSI) is an alternative technique to access blood flow in tissue. This technique has never been patented but was described in scientific publications; for a review see [J. D. Briers, "Laser Doppler, speckle and related techniques for blood perfusion mapping and imaging", Physiol. Meas. 22, R35-R66 (2001)]. This technique is based on the image speckle contrast analysis. Various modifications of this technique were reported but those modifications are mainly focused on the signal processing part rather the measurement principal, which is virtually the same for all variants. The LSI system obtains flow-related information by measuring the contrast of the image speckles formed by the detected laser light. If the sample consists or contains moving particles, e.g. blood cells, the speckle pattern fluctuates. The measured contrast is related to the flow parameters (such as speed and concentration of moving particles) of the investigated object. The contrast value is estimated for a certain integration time (exposure time) of the sensor. The faster the speckle pattern fluctuations the lower the contrast value measured at a given exposure time. The control unit defines the exposure time of the image sensor to determine the range of the measured flow-related data related to the image contrast in Laser Speckle Imaging mode. Here, the integration time defines the range of measured speeds. The use of integrating image detectors is mandatory. Until now only the use of CCD type image sensors were reported for the technique.

The LSI is true real-time imaging technique, however as explained above the LSI signal approach cannot discriminate between concentration of flowing particles and their speed. The laser Doppler imaging provides more information as that the LSI method since with laser Doppler the concentration and speed signals can be measured independently. In LSI those signals are always intricately mixed i.e. it is impossible to deduce from speckle contrast changes in concentration or in speed of moving particles Generally, the LSI approach alone is more likely to be a qualitative indicator of blood flow but not a measuring instrument to accurately investigate physiological phenomena. However as claimed in this invention both concepts have the potential to be used in combination, which may lead to an even better overall performance for a perfusion imaging.

Summarizing the above considerations, we conclude:
a) LDI discriminates between the flow parameters (speed and concentration of moving particles). However LDI is perceived as a slower imaging modality in comparison to LSI.
b) LSI is a fast imaging technique, however the results obtained with this technique have not the information content as LDI i.e. does not allow acquiring particles speed and concentration independently.

SUMMARY OF THE INVENTION

In this invention we describe an instrument that takes into account the advantages of both techniques for accurate and objective monitoring and the real-time imaging of microcirculation in tissue.

The aim of this invention is obtained thanks to a Laser Perfusion Imaging system comprising
a. at least one coherent light source,
b. a light collecting optic,
c. at least one 2D array of integrating photo detectors for receiving the collected light,
d. a control unit,
e. a signal processor unit and
f. a display unit to display the results,
the coherent light source is arranged for illuminating a selected area of interest on a sample for determining flow-related data of said sample, said collected light photo detector being a two dimensional array of randomly addressed integrating photo detectors and is arranged for detecting a laser Doppler signal and/or image speckle signal from said selected area of interest of said sample.

BRIEF DESCRIPTION OF THE DRAWINGS

The description will be better understood thanks to the attached drawings in which:

FIG. 3a shows the perfusion map FIG. 3b shows the blood concentration map FIG. 3c shows the flow speed map, FIG. 3d shows the image of the object.

DETAILED DESCRIPTION OF THE INVENTION

An object of this invention is to propose an instrument for high-speed high-resolution imaging of microcirculation in tissues and to overcome the disadvantages of the prior described instruments or concepts.

A further object of this invention is a high-speed laser Doppler perfusion imaging system which allows digital photography, Doppler signal measurements and image speckle contrast analysis, all performed by a single detector.

An object of this invention is to acquire the signal from a plurality of illuminated spots by individual pixels, to integrate the induced photocurrent in a programmable, adapted way for increasing the signal-to-noise ratio and to process these signals for displaying finally 2D flow-related maps (perfusion, concentration, speed) with a high frame rate.

An object of this invention is to illuminate the sample i.e. biological tissue via a fiberized system in a very homogeneous way, by a fiber, GRIN-lens combination.

A further object of this invention is the use of a 2D matrix of integrating photo detectors that can be addressed randomly (pixel per pixel or in a ROI) with a high access rate. The integrating detectors organized in a 2D randomly addressed array allow a
i) Recording of the interferometric intensity fluctuations induced by detected dynamically scattered light individually for each detector element, ii) Measuring of the contrast (blur) of the image speckles formed by the light reemitted from the object as a function of the integration time, iii) Obtaining a digital photographic image of the object. This image is used for determining the anatomical boundaries associated with the blood flow-maps.

Figure 6:
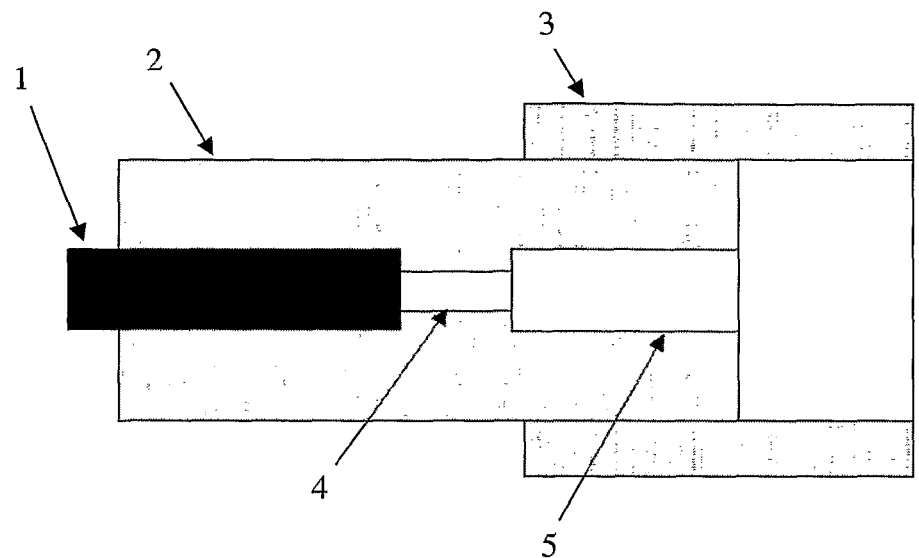
FIG. 6 shows an example of a coherent light source.
Figure 7:
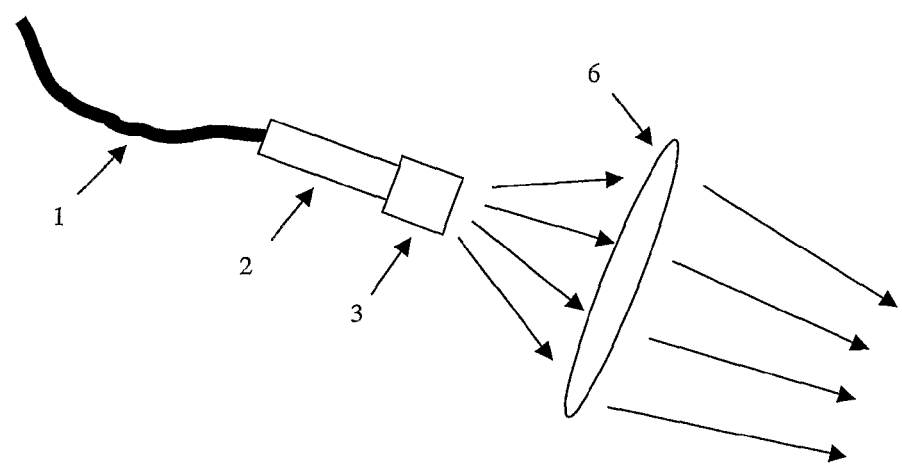
FIG. 7 shows a device for uniform diffuse illumination.

Another object of this invention is the description of a uniform homogeneous illumination of a section of an object of interest using a coherent light source such as an extended laser beam with a uniform intensity profile (see also the drawings FIG. 6 & 7). The illuminating laser beam can scan the sample in a step-wise manner by a step-scanning system to increase the size of the measured area. The part corresponding to the illuminated region of the image received by the sensor is processed by the system. The backscattered light is collected with a light collecting optic on a 2D array of integrating detectors. Two approaches are used to analyze the signal:

i) the laser speckle approach allows performing full-field flow imaging in real-time;

ii) the laser Doppler technique is applied here to increase the obtained results.

Combination of these two techniques allows to decrease the total imaging time and to increase the accuracy of the measurement. Important, that both imaging techniques are performed with a single image sensor.

A further object of this invention is to use the integration time as an additional degree of freedom to measure flow parameters. The use of integrating detectors allows the increase of the photon collection efficiency, which results in an increased SNR (signal/noise ratio) of the measurements. That is of particular importance for the parallel detection concept (full-field detection). Also, the integrating detector allows the flexibility in selecting the integration time to always match the required signal bandwidth to the noise bandwidth reducing in this way the high-frequency noise contributions, therefore effectively increasing the SNR of the measurement.

A further object of this invention is the full-field illumination, where an area of interest is illuminated with an expanded laser beam. The illuminated surface is imaged on the matrix of integrating photo detectors via a light collecting optic with a certain (de-) magnification factor. A sequence of images is acquired during a certain data acquisition time; thus the history of the intensity variations is recorded into the memory for each pixel of the image in a digital format. The frequency content of this signal per pixel is analyzed with FFT algorithm. The total power of the intensity oscillations is proportional to the concentration of moving particles and to the integration time. Therefore the integration time is used as an additional parameter to estimate the speed. The frequency distribution of the intensity oscillations contains information about the speed distribution of moving particles.

A further object of this invention is the signal processing, which comprises the calculations of the flow-related signal (perfusion, concentration, speed) for each pixel of the image according to a predefined algorithm. The flow-related parameters are calculated from both the power spectra of the intensity fluctuations and the image speckle pattern contrast decay. Then, the flow-related maps are displayed on the monitor in real-time.

Figure 1:
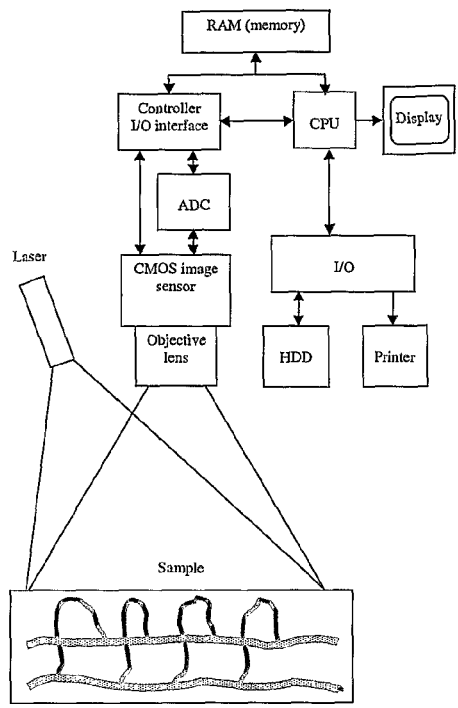
FIG. 1 describes a block diagram of the laser Doppler imaging system modules.

In FIG. 1, it is shown a block diagram of the laser Doppler imaging system modules. It comprises a laser source for illuminating the sample; the backscattered light is collected by an optic and detected by the CMOS image sensor. This signal is converted to a digital signal by the ADC converter and stored in the RAM memory. The control unit also called the Controller I/O Interface, ensures the necessary synchronization and settings of the CMOS image sensor and the link to the RAM memory as well as the signal processor unit or CPU unit. This CPU unit is also involved in the calculation and processing of the digital signal as well as the display onto a display unit and the data storage of the processed data across the I/O unit onto a hard disk HDD or printer.

In the memory (RAM) of the laser perfusion imaging system, in order to process the two type of detections, i.e. Laser Doppler and Laser speckle, two set of parameters are available. Other set of parameters can be available for standard imaging process, e.g. when acquiring the boundaries of the object of interest. The control unit CPU loads the selected parameters set and apply these parameters to the laser perfusion imaging system, i.e. to the light source, the collecting optics and the controller I/O interface. The CPU program related to the current processing is also loaded in the memory of said processing unit.

The signal sampling frequency is inversely proportional to the acquisition time of one sub-frame. The sub-frame sampling rate of the sensor depends on its size and the pixel clock frequency. In our case it was fixed at 40 MHz for the optimum performance speed/quality; higher pixel rates increase the noise level. The size of the sampled sub-frame finally defines the sampling frequency of the imager. E.g. for the sensor we used: for 256×4 pixels sub-frame the sampling frequency is 30 kHz, 256×6 pixels—20 kHz, 256×8 pixels—14 kHz, etc.

To obtain one flow map over a Region Of Interest (ROI), which is in our case 256×256 pixels, the ROI must be subdivided in smaller areas (e.g. in 32 sub-frames of 256×8 size) and scanned electronically. From 32 to 512 samples are obtained for each sub-frame, thus the intensity fluctuations history is recorded for each pixel of this predefined ROI.

The signal processing comprises the calculation of the zero-moment ($M_0$) and the first-moment ($M_1$) of the spectral power density $S(v)$ of the intensity fluctuations $I(t)$ for each pixel. The zero-moment is related to the average concentration, $<C>$, of moving particles in the sampling volume. The first moment (flux or perfusion) is proportional to the root-mean-square speed of moving particles, $V_{rms}$, times their average concentration:

$$\text{Concentration} = \langle C \rangle \propto M_0 = \int_0^\infty S(v) dv$$

$$\text{Perfusion} = \langle C \rangle V_{rms} \propto M_1 = \int_0^\infty v S(v) dv.$$

$$S(v) = \left| \int_0^\infty I(t) \exp(-i 2\pi v t) dt \right|^2$$

Here v is a frequency of the intensity fluctuations induced by the Doppler shifted photons. We calculated the power spectrum using FFT algorithm applied to recorded signal variations at each sampled pixel of ROI. The noise subtraction is performed from the calculated spectra by setting a threshold level on the amplitude of the spectral components. This filtering is applied to reduce the white noise (e.g. thermal and read-out noises) contribution to the signal. Thereafter the perfusion, concentration and speed maps are calculated and displayed on computer monitor.

Figure 2A:
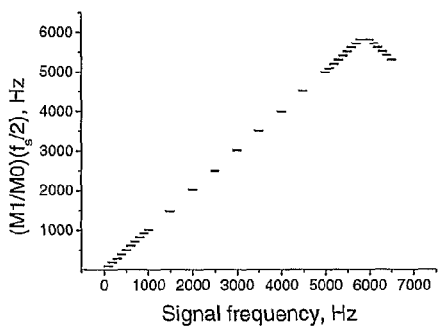
FIG. 2a shows the moment ratio $M_1/M_0$ (velocity) imager response on the change of the measured signal frequency.

In FIG. 2(a) the moment ratio $M_1/M_0$ as indicated above shows the speed response of the imager as a function of the input signal frequency. The input signal of 10% modulating depth $AC_{rms}/DC$ was measured for the frequency range from 100 to 6500 Hz. A linear dependence of the moment ratio $M_1/M_0$ imager response is found up to the Nyquist frequency;

that matches well to the theoretical expectation. Effectively, the measured $(M_1/M_0)f_s$ value should be equal to the signal frequency, which is clearly seen from the results. Beyond 6000 Hz, a decay in the imager response is observed due to an aliasing effect. It should be noted that the digital image sensors do not usually include antialiasing circuitry in their design; therefore the aliasing effect is virtually unavoidable in the imager. An antialiasing filter must be employed before the signal is digitized. It usually does not have an effect applying a low pass filter on the digitized signal because the aliasing effects occur before of the sampling process. Any aliasing effects would already be stored in the digitized signal and cannot be removed by low pass filtering as the effects appear as low frequencies in the signal. It should be noticed in addition, that the integrating sensor reduces the aliasing effect by suppressing the amplitude of the higher frequency components.

Figure 2B:
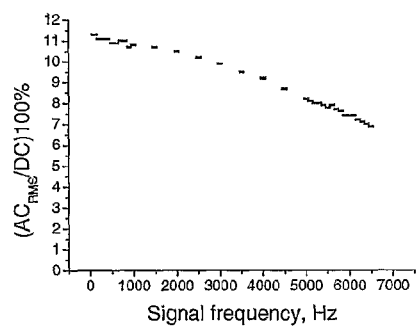
FIG. 2b shows the (concentration, $M_0$) imager response on the change of the measured signal frequency.

In FIG. 2(b) the $AC_{RMS}$/DC ratio of the imager as a function of the input signal frequency is shown. The $AC_{RMS}$/DC value is proportional to the square root of $M_0$ moment. The decay in the $\sqrt{M_0}$ imager response is due to the non-zero integration time of the detectors. This pendence is very similar to the frequency response of a basic low pass filter RC-circuit with a time constant defined by equation (9); see also equation (11). The decay of a factor of 0.5 for the RC-circuit is typical. For the integrating sensor the signal response near the cut-off frequency is even smaller and being approximately of 0.7 of its maximum.

Figure 2C:
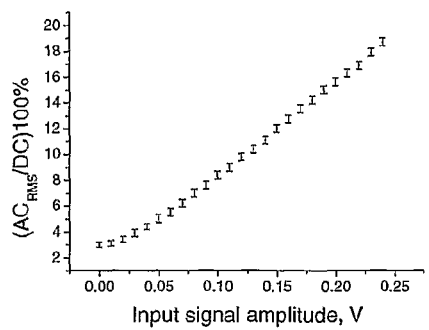
FIG. 2c shows the (concentration) imager response on the change of the measured signal amplitude.

In FIG. 2(c) the imaging system $\sqrt{M_0}$ response to the amplitude changes of the input signal is shown. The input signal frequency was fixed at 3000 Hz. The imager signal amplitude response shows an expected linear dependence. At low amplitudes of the input signal the imager response demonstrates a nonlinearity caused by the noise.

Figure 2D:
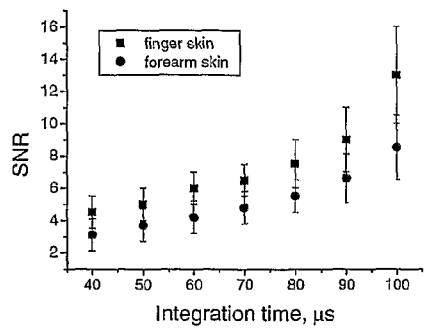
FIG. 2d shows a signal to noise ration of the system for measurements on finger and forearm skin. The standard deviations for each measured values are also shown in the graph.

Finally in FIG. 2(d) the SNR (signal to noise ratio) of the system for measurements on a finger and on the inner forearm skin is shown. The standard deviations for each measured values are also given.

A further object of this invention is to use different exposure times for different photo detectors or pixel areas for increasing the intra-scene dynamic range of the sensor. This is applied for measuring the samples with highly reflective parts.

A further object of this invention is to describe a Laser Perfusion Imaging system characterized by two imaging modes of operation: laser Doppler imaging (LDI) and laser Speckle Imaging (LSI). The said imaging modes are chosen depending on the requirement of a particular application. The LDI mode is characterized by higher accuracy; the LSI mode is characterized by higher speed. In the said imaging system, during the measurements the imaging mode can alter between LDI and LSI.

A further object of this invention is the use of an integrating instead of a non-integrating detector as used in the prior mentioned publications and patents.

There exist two basically different concepts in CMOS image sensor technology for capturing photons on the detector: non-integrating and integrating detectors.

In non-integrating detector, the photon flux is continuously converted into an electrical current i.e. the output signal. To obtain images, the detector array is read-out instantaneously by means of sequential photoelectrical scanning. One pixel detects only the photons that are captured during the sampling time of the pixel:

$$\Delta t = \frac{T_{tot}}{N}. \quad (1)$$

Here $T_{tot}$ is a time to read-out all N pixels of the frame (or sub-frame). Thus, during $\Delta t$ one pixel detects X photons:

$$X_{non\_int} \propto \frac{P_{tot}}{N} \Delta t. \quad (2)$$

Here $P_{tot}$ is the total illumination power.

In the integrating detector concept the total photon current is integrated as a charge when the detector captures photons. All charges are accumulated in a small capacitor, which at the end of the exposure time interval is red out. The charge is then converted into the output signal linearly proportional to the number of photons captured by the detecting pixel. In addition each pixel collects photons during the time other photo detectors are read-out (rolling shutter mode) or all photo detectors collect photons during the exposure time interval and they are read-out immediately thereafter (global shutter mode). The maximum integration time (or exposure time) is equal to the time to read-out N pixels, $T_{int}=T_{tot}$. Therefore, the number of photons detected by one pixel of an integrating detector array is $$X_{non\_int} \propto \frac{P_{tot}}{N} T_{tot} \quad (3)$$

For both systems the signal to noise ratio (SNR) is determined by the number of detected photons X:

$$SNR \propto \sqrt{X}. \quad (4)$$

So the advantage in the SNR for the integrating system is $$\frac{SNR_{int}}{SNR_{non\_int}} = \sqrt{N} \quad (5)$$

Here we have compared two imaging systems, one with integrating detector array and one with a non-integrating (scanning) detector array. Up to now we have assumed equal detector noise for both imagers, which is not always true. For completing these considerations, the influence of the temporal noise on SNR of each imaging system should also be considered.

For both types of sensors, the minimum noise floor consists of thermal noise, TN, and shot noise, SN, caused by the average photocurrent plus average dark current, $\langle I \rangle = \langle I_{photo} \rangle + \langle I_{dark} \rangle$, in the circuit:

$$TN = \langle i_{TN}^2 \rangle = \frac{4 \cdot k \cdot T \cdot B_n}{R} \quad (6)$$

$$SN = \langle i_{SN}^2 \rangle = 2 \cdot q \cdot \langle I \rangle \cdot B_n.$$

Here k is Boltzmann's constant, e is the charge of an electron, T is the temperature in degrees Kelvin, $B_n$ is the noise equivalent bandwidth, and R is the load resistance The value of the load resistance is determined by the upper cutoff frequency $f_s$ required to pass the signal $$R = \frac{1}{2\pi \cdot C \cdot f_s}, \quad (7)$$

where C is the capacitance of the photo detector. The signal-to-noise ratio (SNR) is then $$SNR = \frac{\langle i_s^2 \rangle}{2 \cdot q \cdot \langle I \rangle \cdot B_n + 8\pi \cdot k \cdot T \cdot C \cdot f_s \cdot B_n}. \quad (8)$$

First, consider the non-integrating devices. In general, the noise bandwidth and the signal bandwidth are not the same. If the upper cutoff frequency is determined by a single RC time constant the signal bandwidth and the noise bandwidth are accordingly $$f_s = \frac{1}{2\pi \cdot R \cdot C} \quad (9)$$

$$B_n = \frac{1}{4 \cdot R \cdot C} = \frac{\pi}{2} f_s.$$

Thus for the non-integrating detector the SNR is $$SNR_{non\text{-}int} = \frac{\langle i_s^2 \rangle}{\pi \cdot q \cdot \langle I \rangle \cdot f_s + 4\pi^2 \cdot k \cdot T \cdot C \cdot f_s^2}. \quad (10)$$

Second, for the integrating detector, the SNR is expressed as before, equation (8), except that the noise bandwidth is now defined as $B_n = 1/(2 \cdot T_{int})$, where $T_{int}$ is the time interval between successive readout cycles of the diodes (the integration time or exposure time interval). The bandwidth of the Laser Perfusion Imaging system is adjusted to the measured signal bandwidth by means of setting-up the exposure time of the image sensor to a predetermined value defined by the signal bandwidth. Therefore, to match the signal bandwidth the integration time is determined by $$B_n = \frac{1}{2 \cdot T_{int}} = f_s. \quad (11)$$

Now we find for SNR of the integrating detector $$SNR_{int} = \frac{\langle i_s^2 \rangle}{2 \cdot q \cdot \langle I \rangle \cdot f_s + 8\pi \cdot k \cdot T \cdot C \cdot f_s^2} = \frac{\pi}{2} SNR_{non\text{-}int}. \quad (12)$$

Thus, at the same photocurrent, the SNR of the integrating detector is about a factor of 1.5 better than for the non-integrating device.

Finally, using equation (5) and equation (12) we find that for the scan case, where only one pixels of the image is measured at a time, the SNR of the integrating detector array can be increased by a factor of:

$$\frac{SNR_{int}}{SNR_{non\_int}} = \frac{\pi}{2}\sqrt{N}. \quad (13)$$

The above considerations concern the fundamental difference between the detectors, however some technological features that influence the detector performance should also be mentioned.

One problem encountered in non-integrating detector is the dependence of the time constant on the signal level; that makes the non-integrating detector bandwidth to be dependent on the signal level. This problem could be in principle eliminated but on the expense of the increased noise floor caused by the on-chip integrated amplifier circuit.

As for the integrating system, an additional advantage available here is the possibility of reducing the effect of the thermal noise. This can be achieved by a well-known correlated double sampling signal processing method. Also, the read-out noise of the non-integrating sensor is usually about an order of magnitude higher than for the integrating one.

Another essential advantage of the integrating detector concept is the flexibility in selecting the integration time in order to match the required signal bandwidth. Since both shot and thermal noises are distributed over a wide frequency range, reducing effectively the noise bandwidth reduces the noise contribution of the measurement. Therefore the integration time can be used as an additional degree of freedom for an optimized high- speed Laser Perfusion Imaging system.

The Laser Perfusion Imaging system as described above, may further comprise an auto-mode operation where the optimal settings for the imaging system (gain, bandwidth, exposure time, etc) are set autonomously depending on the measured object properties (velocity, illumination conditions, etc.) and the auto-settings are determined by the object image and analysis based on flow-map images histograms but not limited to.

Figure 3:
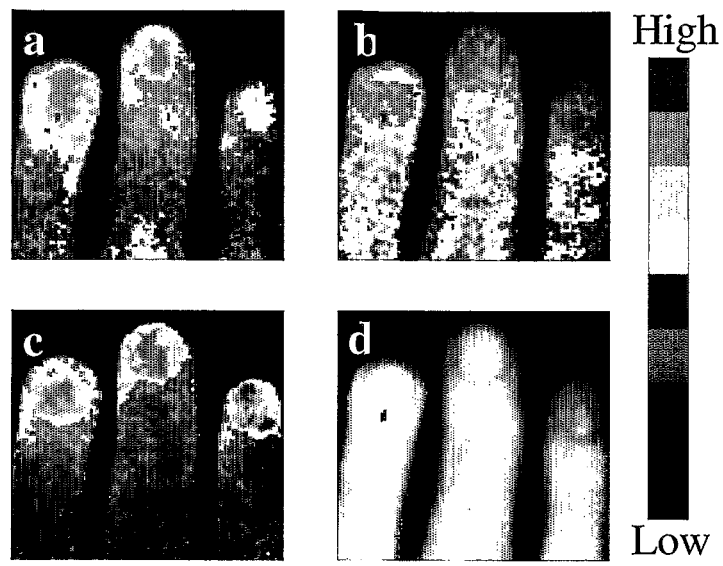
FIG. 3 shows 256×256 pixels flow-related maps obtained with the new imager on finger skin

In FIG. 3 flow-related images obtained of a finger for a healthy person are shown. An image of 256×256 pixels was obtained with the LDI imager: FIG. 3 a) perfusion map [Low=1500 a.u.; High=3000 a.u.]; FIG. 3 b) blood concentration map [Low=150 a.u.; High=300 a.u.]; FIG. 3 c) flow speed map [Low=500 a.u.; High=1500 a.u.]; FIG. 3 d) standard digital image of the finger. The total imaging time was 3.5 seconds.

The images are obtained for the imager settings for the bandwidth from 100 to 6000 Hz with 100 Hz resolution; the integration time was 82 μs. A smoothing filter was applied to the row images: the shown value of each pixel was obtained by averaging the raw-values of 8 neighboring pixels. The flow images (perfusion, concentration, speed) are false-color coded with 9 colors. This coding is relative and does not mean that measured perfusion value coded by e.g. red is equal to the value for concentration or speed coded by the red color. The images clearly show the difference in speed and concentration distributions measured on the fingers.

Figure 4:
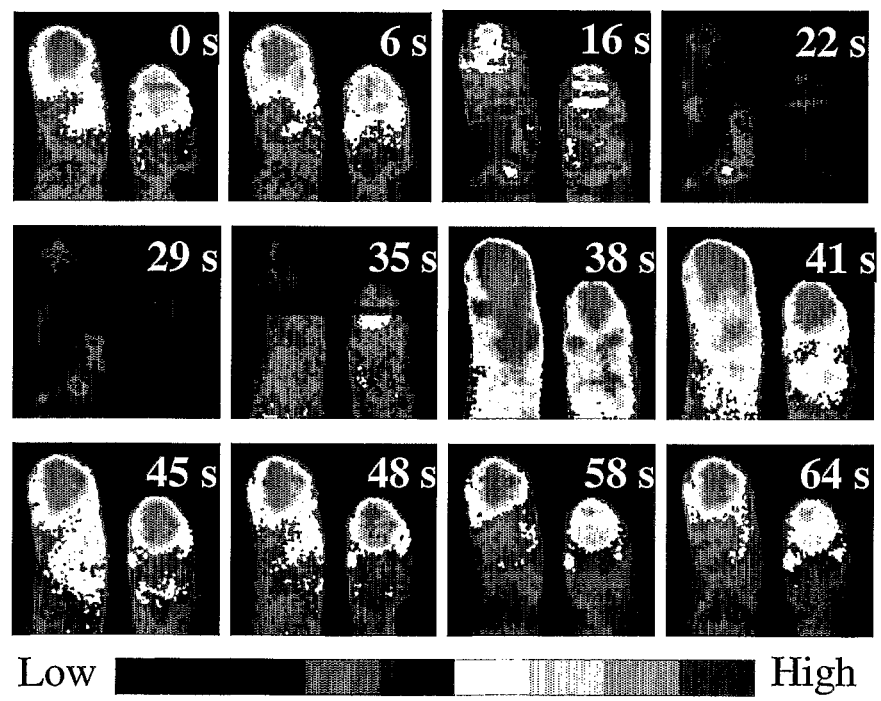
FIG. 4 shows time-sequence of images of an artery occlusion experiment.

The perfusion images shown in FIG. 4 are obtained during an artery occlusion experiment. The imager settings were the same as for the measurements described in FIG. 3. This example demonstrates the performance of the imager in the continuous imaging mode. The images were taken sequentially with a time difference of 3.5 seconds, comparable to the imaging time for one image. The selected images ordered in a matrix of 4×3 images visualize the perfusion time sequence before, during and after the occlusion. As expected, there is a decrease of perfusion during the occlusion. After release of the occlusion the local perfusion shows an "overshooting" i.e. a marked increased perfusion above the initial perfusion; this physiological effect is known as reactive hyperemia. Shortly after, the perfusion returns to the initial state.

Figure 5:
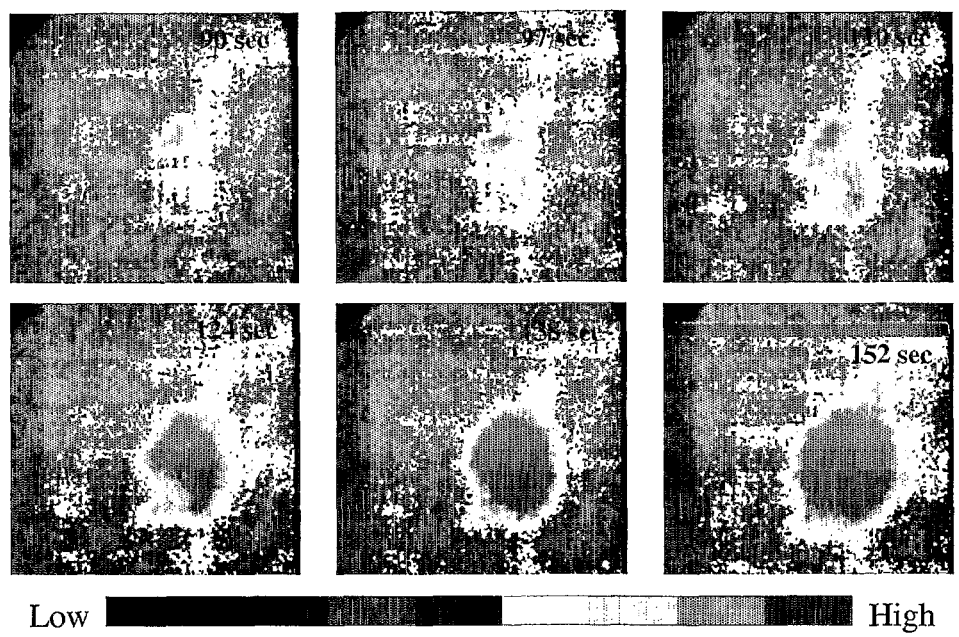
FIG. 5 shows perfusion images obtained with the high-speed laser Doppler imager.

The effect of a topical applied agent is clearly seen on the images shown in FIG. 5. A small amount of this agent penetrates and crosses the skin layers and induces a perfusion increase within a few minutes. The images show the time trace of the penetration history until the heavily increased subcutaneous perfusion response.

The perfusion images (256×256 pixels) are obtained with the high-speed laser Doppler imager. The imaging area is 5.5×5.5 cm$^2$. The agent was applied on the skin of the inner side of the forearm. The perfusion images show the blood flow changes in time: in 90, 97, 110, 124, 138, and 152 seconds after the topical agent was applied to the skin. Imaging time is approx. 3.5 seconds per image. Here, the "Low" corresponds to a perfusion value of 500 [arbitrary units] and "High" to a perfusion value of 2500 [arbitrary units].

FIG. 6 shows details of the fiberized illumination device for a uniform sample illumination. This comprises an optical fiber (1), a mechanical holder (2), an outer protection ring (3), the fiber core (4), and a GRIN lens (5).

FIG. 7 shows the uniform diffuse illumination device. This comprises an optical illumination as described in FIG. 6 and a further focusing lens (4).

The present invention is not limited to visualize perfusion, flow velocities and concentration of blood particles, but is also applicable to any field where moving particles interact with coherent light and where this coherent light is superimposed with coherent light coming from non-moving particles. This is the case in water, oil, air etc where the physical i.e. convective, thermal perturbations or laminar-turbulent flow changes but not limited to these examples create particles speed or concentration distributions within the measured flow.

What is claimed is:

1. A Laser Perfusion Imaging system comprising:
   at least one coherent light source configured to illuminate a selected area of interest of an object for determining flow-related data of the selected area;
   a light collecting optic;
   at least one image sensor including a randomly addressed 2D array of integrating photo detectors that receive collected light intensity, the at least one image sensor being configured to detect a laser Doppler signal from the selected area of interest of the object;
   a control unit;
   a signal processor unit; and
   a display unit configured to display results,
   wherein the integrating photo detectors are configured to integrate a charge when the detectors capture photons, said charge being subsequently converted into an output signal linearly proportional to the number of photons captured by each detecting pixel.

2. The Laser Perfusion Imaging system according to claim 1, wherein the at least one image sensor is configured to perform both digital image photography, and a Doppler signal measurement.

3. The Laser Perfusion Imaging system according to claim 2, wherein a photographic image of the object taken with the at least one image sensor is associated with flow-maps and anatomical boundaries of the object.

4. The Laser Perfusion Imaging system according to claim 1, wherein all photo detectors of the at least one image sensor accumulate a photo-charge during an exposure time interval and are readable after the exposure time interval has elapsed.

5. The Laser Perfusion Imaging system according to claim 1, wherein a preselected part of the photo detectors of the at least one image sensor are readable during a time interval whereas a remaining part of the photo detectors accumulate the charge during a same time interval.

6. The Laser Perfusion Imaging system according to claim 1, wherein different exposure times are used for different parts of the photo detectors.

7. The Laser Perfusion Imaging system according to claim 1, wherein the at least one coherent light source includes fiberized and free space optical components for achieving a homogenous illumination field.

8. The Laser Perfusion Imaging system according to claim 1, wherein the at least one coherent light source includes a laser and an optical fiber, the optical fiber being ended with a GRIN lens.

9. The Laser Perfusion Imaging system according to claim 1, wherein the at least one coherent light source is further configured to illuminate a second selected area by displacing the illumination from the illuminated selected area of interest in a programmable step-wise manner by a step-scanning system.

10. The Laser Perfusion Imaging system according to claim 1, wherein the at least one image sensor is connected to the signal-processing unit that comprises a signal and image processor connected to a data memory and a data input/output interface, the signal and image processor is configured to determine the flow-related data from the area of interest of the object for each photo detector in the image sensor.

11. The Laser Perfusion Imaging system according to claim 1, wherein the signal processor unit is configured to calculate the flow-related data for each photo detector from at least a zero moment of collected light intensities and/or a moment ratio of the collected light intensities.

12. The Laser Perfusion Imaging system according to claim 1, further comprising an adjustment unit configured to adjust a measured signal bandwidth by setting-up a sampling rate and/or exposure time of the image sensor to a predetermined value.

13. A method for acquiring flow related images of an object by a Laser Perfusion Imaging system, comprising:
   illuminating the object containing a flow with a coherent light source;
   capturing backscattered light from the object with a collecting optic;
   detecting a sequence of images with an image sensor including a randomly addressed 2D array of integrating photo detectors, the integrating photo detectors being configured to integrate a charge when the detectors capture photons, said charge being subsequently converted into an output signal linearly proportional to the number of photons captured by each detecting pixel;
   processing the sequence of images and performing a moment analysis for extracting flow related data; and
   producing a displayable image resulting from the moment analysis.

14. The method according to claim 13, further comprising:
   acquiring a digital photographic image of the object; and
   defining anatomical boundaries of the object and associating them with the displayable image.

15. The method according to claim 13, further comprising:
   reading out a preselected part of the photo detectors after an exposure time while a remaining part of the photo detectors continue to acquire charges.

16. The method according to claim 13, further comprising:
   reading out all photo detectors after accumulation of charges during an exposure time.

17. The method according to claim 13, further comprising:
   selecting an area of interest of the object by step-wise displacing the coherent light source; and
   processing a corresponding part of the backscattered light on the image sensor.

18. The method according to claim 13, wherein the object illuminated is a biological sample.

* * * * *

UNITED STATES PATENT AND TRADEMARK OFFICE
CERTIFICATE OF CORRECTION

| | | |
|---|---|---|
| PATENT NO. | : 8,480,579 B2 | Page 1 of 1 |
| APPLICATION NO. | : 11/912224 | |
| DATED | : July 9, 2013 | |
| INVENTOR(S) | : Alexandre Serov et al. | |

It is certified that error appears in the above-identified patent and that said Letters Patent is hereby corrected as shown below:

On the title page, Item (73), the Assignee's Information is incorrrect. Item (73) should read:

--(73) Assignee: Ecole Polytechnique Fédérale de Lausanne (EPFL), Lausanne (CH)--

Signed and Sealed this
Tenth Day of September, 2013

Teresa Stanek Rea
*Acting Director of the United States Patent and Trademark Office*